US00PP30679P2

(12) United States Plant Patent
Graff

(10) Patent No.: US PP30,679 P2
(45) Date of Patent: Jul. 9, 2019

(54) POINSETTIA PLANT NAMED 'Q103'

(50) Latin Name: ***Euphorbia pulcherrima* Willd.**
Varietal Denomination: Q103

(71) Applicant: Poul Graff, Sabro (DK)

(72) Inventor: Poul Graff, Sabro (DK)

(73) Assignee: Graff Breeding A/S, Sabro (DK)

( * ) Notice: Subject to any disclaimer, the term of this patent is extended or adjusted under 35 U.S.C. 154(b) by 0 days.

(21) Appl. No.: 15/932,704

(22) Filed: Apr. 10, 2018

(51) Int. Cl.
*A01H 5/02* (2018.01)

(52) U.S. Cl.
USPC ..... Plt./303

(58) Field of Classification Search
USPC ..... Plt./303
See application file for complete search history.

*Primary Examiner* — Annette H Para
(74) *Attorney, Agent, or Firm* — C. A. Whealy

(57) ABSTRACT

A new and distinct cultivar of Poinsettia plant named 'Q103', characterized by its compact, upright and uniformly mounding plant habit; moderately vigorous growth habit; freely branching habit; dark green-colored leaves; large and full inflorescences with numerous light orange to yellow orange-colored flower bracts; and excellent post-production longevity.

2 Drawing Sheets

Botanical designation: *Euphorbia pulcherrima* Willd.
Cultivar denomination: 'Q103'.

BACKGROUND OF THE INVENTION

The present invention relates to a new and distinct cultivar of Poinsettia plant, botanically known as *Euphorbia pulcherrima* Willd. and hereinafter referred to by the name 'Q103'.

The new Poinsettia plant is a product of a planned breeding program conducted by the Inventor in Sabro, Denmark. The objective of the breeding program is to create uniform and freely-branching Poinsettia plants with attractive inflorescences and good postproduction longevity.

The new Poinsettia plant originated from a cross-pollination made by the Inventor in August, 2015 in Sabro, Denmark of a proprietary selection of *Euphorbia pulcherrima* Willd. identified as code number 11_13, not patented, as the female, or seed, parent with a proprietary selection of *Euphorbia pulcherrima* Willd. identified as code number 2012-0099, not patented, as the male, or pollen, parent. The new Poinsettia plant was discovered and selected by the Inventor as a single flowering plant within the progeny of the stated cross-pollination in a controlled greenhouse environment in Sabro, Denmark in May, 2016.

Asexual reproduction of the new Poinsettia plant by terminal vegetative cuttings in a controlled greenhouse environment in Sabro, Denmark since September, 2016 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Q103'. These characteristics in combination distinguish 'Q103' as a new and distinct Poinsettia plant:

1. Compact, upright and uniformly mounding plant habit.
2. Moderately vigorous growth habit.
3. Freely branching habit.
4. Dark green-colored leaves.
5. Large and full inflorescences with numerous light orange to yellow orange-colored flower bracts.
6. Excellent post-production longevity.

Plants of the new Poinsettia can be compared to plants of the female parent selection. In side-by-side comparisons, plants of the new Poinsettia differ primarily from plants of the female parent selection in flower bract color as flower bracts of plants of the female parent selection are yellow in color.

Plants of the new Poinsettia can be compared to plants of the male parent selection. In side-by-side comparisons, plants of the new Poinsettia differ primarily from plants of the male parent selection in flower bract color as flower bracts of plants of the male parent selection are lighter yellow orange in color.

Plants of the new Poinsettia can also be compared to plants of *Euphorbia pulcherrima* Willd. 'NPCW10164', disclosed in U.S. Plant Pat. No. 22,597. In side-by-side comparisons, plants of the new Poinsettia differ primarily from plants of 'NPCW10164' in the following characteristics:

1. Plants of the new Poinsettia are more freely branching than plants of 'NPCW10164'.
2. Flower bracts of plants of the new Poinsettia are slightly shorter than flower bracts of plants of 'NPCW10164'.
3. Flower bracts of plants of the new Poinsettia are light orange to yellow orange in color whereas flower bracts of plants of 'NPCW10164' are red in color.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet is a side perspective view of a typical flowering plant of 'Q103' grown in a container.

The photograph at the top of second sheet is a close-up view of a typical dissected inflorescence of 'Q103'.

The photograph at the bottom of second sheet is a close-up view of the lower and upper surfaces of typical leaves of 'Q103'.

DETAILED BOTANICAL DESCRIPTION

The aforementioned photographs and following observations, measurements and values describe plants grown during the winter in 13-cm containers in a glass-covered greenhouse in Sabro, Denmark and under cultural practices typical of commercial Poinsettia production. During the production of the plants, day temperatures ranged from 20° C. to 25° C., night temperatures ranged from 19° C. to 21° C. and light levels ranged from 40 to 50 klux. Plants were pinched one time eight weeks after planting and plants were 20 weeks old when the photographs and the description were taken. In the description, color references are made to The Royal Horticultural Society Colour Chart, 2001 Edition, except where general terms of ordinary dictionary significance are used.

Botanical classification: *Euphorbia pulcherrima* Willd. 'Q103'.

Parentage:

*Female, or seed, parent*.—Proprietary selection of *Euphorbia pulcherrima* Willd. identified as code number 11_13, not patented.

*Male, or pollen, parent*.—Proprietary selection of *Euphorbia pulcherrima* Willd. identified as code number 2012-0099, not patented.

Propagation:

*Type*.—Terminal vegetative cuttings.

*Time to initiate roots, summer*.—About three weeks at temperatures about 24° C.

*Time to initiate roots, winter*.—About four weeks at temperatures about 24° C.

*Time to produce a rooted young plant, summer*.—About eight weeks at temperatures about 24° C.

*Time to produce a rooted young plant, winter*.—About ten weeks at temperatures about 24° C.

*Root description*.—Medium in thickness, fleshy; color, close to 161D, actual color of the roots is dependent on substrate composition, water quality, fertilizer type and formulation, substrate temperature and physiological age of roots.

*Rooting habit*.—Freely branching; dense.

Plant description:

*Plant and growth habit*.—Compact, upright and uniformly mounded plant habit; inverted triangle with rounded crown; large full inflorescences positioned above the foliar plane; moderately vigorous growth habit and moderate growth rate.

*Plant height, soil level to tope of foliar plane*.—About 15 cm to 30 cm.

*Plant height, soil level to tope of floral plane*.—About 15 cm to 35 cm.

*Plant diameter or spread*.—About 30 cm to 50 cm.

*Lateral branch description*.—Branching habit: Freely branching habit, about three to six lateral branches develop after pinching. Length: About 15 cm to 30 cm. Diameter: About 3 mm to 6 mm. Internode length: About 1 cm to 5 cm. Strength: Strong. Texture and luster: Smooth, glabrous; semi-glossy. Angle: Mostly upright. Color, developing: Close to N144D. Color, developed: Close to 138A.

*Leaf description*.—Arrangement and appearance: Alternate, simple. Length: About 12 cm to 16 cm. Width: About 9 cm to 12 cm. Shape: Broadly ovate. Apex: Acuminate. Base: Slightly cordate. Margin: Entire, shallowly lobed. Venation pattern: Pinnate. Aspect: Mostly flat. Texture and luster, upper and lower surfaces: Rugose, glabrous; leathery; matte. Color: Developing leaves, upper surface: Close to 136A. Developing leaves, lower surface: Close to 137C. Fully expanded leaves, upper surface: Close to N189A; venation, close to 189A. Fully expanded leaves, lower surface: Close to 189A; venation, close to 191A. Petioles: Length: About 6 cm to 8 cm. Diameter: About 3 mm to 5 mm. Texture and luster, upper and lower surfaces: Smooth, glabrous; semi-glossy. Color, upper and lower surfaces: Close to N144A.

Inflorescence description:

*Inflorescence type and habit*.—Large full inflorescences are compound corymbs of cyathia with light orange to yellow orange-colored flower bracts subtending the cyathia; one inflorescence per lateral branch with inflorescences positioned above and beyond the foliar plane.

*Fragrance*.—None detected.

*Natural flowering season*.—Plants flower naturally during the autumn and winter under long nyctoperiod conditions; inflorescence initiation and development can be induced under artificial long nyctoperiod conditions; early flowering habit, response time is about eight to nine weeks after start of long nyctoperiod conditions.

*Post-production longevity*.—Excellent post-production longevity; plants of the new Poinsettia maintain good substance and bract color for about six to eight weeks under interior conditions; flower bracts persistent.

*Inflorescence diameter*.—About 15 cm to 25 cm.

*Inflorescence height*.—About 3 cm to 5 cm.

*Flower bracts*.—Quantity per inflorescence: About 15 to 25. Length: About 9 cm to 12 cm. Width: About 7 cm to 9 cm. Shape: Ovate. Apex: Acuminate. Base: Slightly cordate. Margin: Entire, occasionally shallowly lobed. Venation: Pinnate. Texture and luster, upper and lower surfaces: Rugose, glabrous; velvety; matte. Aspect: Mostly horizontal to slightly downward. Color: Developing (transitional) bracts, upper surface: Variable sectors, close to 22B and 137A. Developing (transitional) bracts, lower surface: Variable sectors, close to 22B and 146A. Fully expanded bracts, upper surface: Close to 26B; small random spots, close to N30A; color becoming closer to 22A with spots, close to 31C, with development. Fully expanded bracts, lower surface: Close to 22B; color becoming closer to 22C with spots, close to 31C, with development. Flower bract petioles: Length:

About 1 cm to 3 cm. Diameter: About 2 mm to 4 mm. Texture, upper and lower surfaces: Smooth, glabrous. Color, upper and lower surfaces: Close to N144A.

*Cyathia*.—Quantity per corymb: About 8 to 15. Length: About 5 mm to 10 mm. Width: About 4 mm to 6 mm. Shape: Rounded. Color, developing, inner surface: Close to 145C. Color, developing, outer surface: Close to 146A. Color, fully developed, inner surface: Close to 157A. Color, fully developed, outer surface: Close to 138A. Nectaries: Quantity per cyathium: Typically one. Length: About 3 mm to 4 mm. Diameter: About 2 mm to 5 mm. Shape: Lanceolate. Texture, inner and outer surfaces: Smooth, glabrous. Color, developing, inner surface: Close to 142D. Color, developing, outer surface: Close to 14B. Color, fully developed, inner surface: Close to 14B. Color, fully developed, outer surface: Close to 16A.

*Peduncles*.—Length: About 3 mm to 5 mm. Diameter: About 2 mm to 5 mm. Strength: Strong. Texture and luster: Smooth, glabrous; semi-glossy. Angle: Mostly upright. Color: Close to 138A.

*Reproductive organs*.—Stamens: Quantity per cyathium: About 50. Filament length: About 1 mm to 5 mm. Filament color: Close to 157A. Anther shape: Reniform. Anther length: About 1 mm. Anther color: Close to 11B. Amount of pollen: Scarce. Pollen color: Close to 11A. Pistils: Quantity per cyathium: Typically one. Pistil length: About 2 mm to 4 mm. Style length: About 1 mm to 3 mm. Style color: Close to 157A. Stigma diameter: About 3 mm. Stigma shape: Five-parted. Stigma color: Close to 185A. Ovary color: Close to 138A. Seeds and fruits: Seed and fruit production has not been observed on plants of the new Poinsettia to date.

Disease & pest resistance: To date, plants of the new Poinsettia have not been shown to be resistant to pathogens and pests common to Poinsettia plants.

Temperature tolerance: Plants of the new Poinsettia have been observed to tolerate temperatures ranging from about 12° C. to about 35° C.

It is claimed:

1. A new and distinct Poinsettia plant named 'Q103' as illustrated and described.

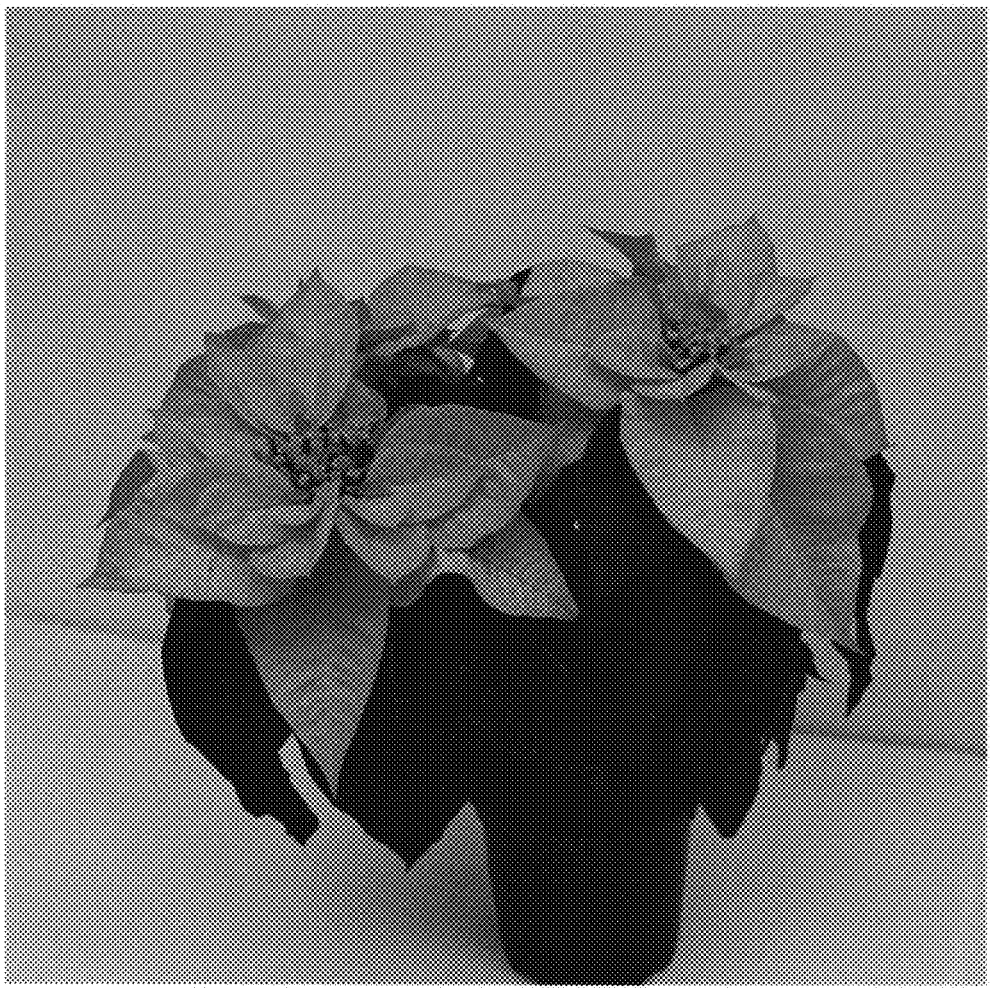

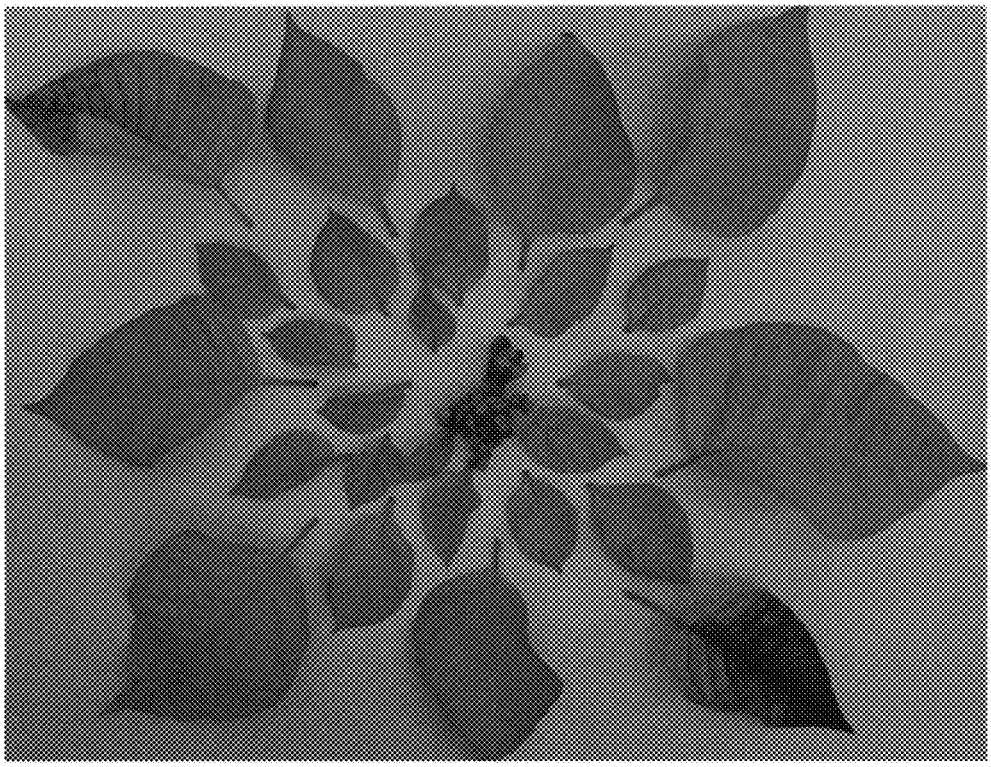
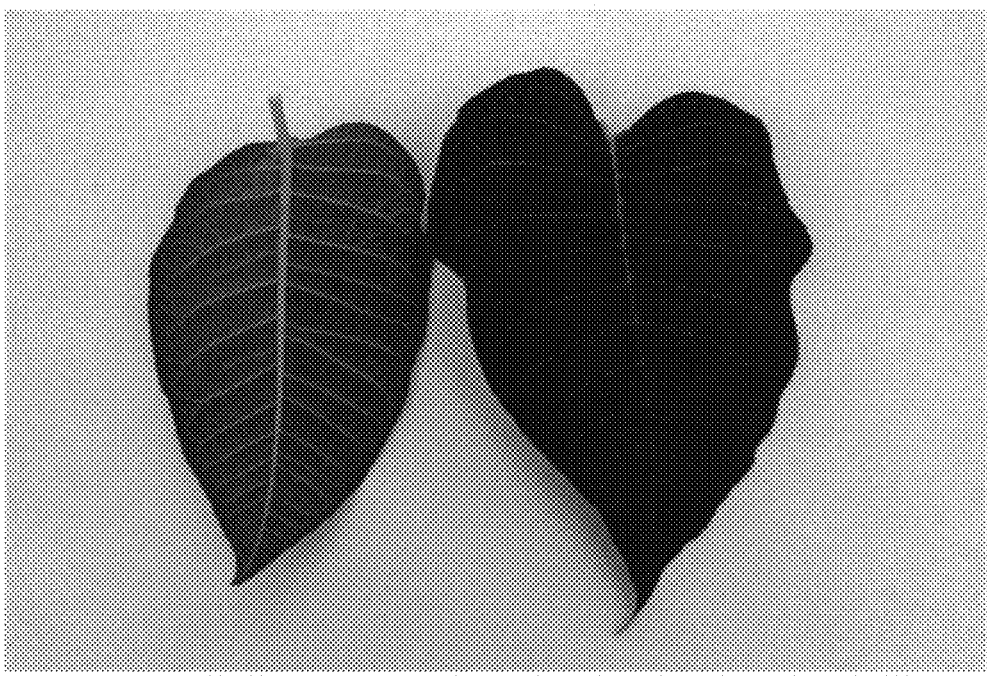

* * * * *